United States Patent
Wang

(10) Patent No.: US 8,197,543 B2
(45) Date of Patent: Jun. 12, 2012

(54) SPINAL PROSTHESES

(76) Inventor: Dajue Wang, Aylesbury (GB)

( * ) Notice: Subject to any disclaimer, the term of this patent is extended or adjusted under 35 U.S.C. 154(b) by 1002 days.

(21) Appl. No.: 11/719,699

(22) PCT Filed: Nov. 21, 2005

(86) PCT No.: PCT/GB2005/004486
§ 371 (c)(1),
(2), (4) Date: May 18, 2007

(87) PCT Pub. No.: WO2006/054111
PCT Pub. Date: May 26, 2006

(65) Prior Publication Data
US 2009/0149955 A1   Jun. 11, 2009

(30) Foreign Application Priority Data
Nov. 20, 2004  (GB) .................................. 0425546.9

(51) Int. Cl.
*A61F 2/44* (2006.01)
(52) U.S. Cl. ..................................... 623/17.11; 606/246
(58) Field of Classification Search .... 623/17.11–17.16; 606/246–249
See application file for complete search history.

(56) References Cited

U.S. PATENT DOCUMENTS

| | | | |
|---|---|---|---|
| 3,867,728 A * | 2/1975 | Stubstad et al. ........... | 623/17.16 |
| 4,932,975 A | 6/1990 | Main et al. | |
| 5,147,404 A | 9/1992 | Downey | |
| 5,674,296 A | 10/1997 | Bryan et al. | |
| 5,755,797 A * | 5/1998 | Baumgartner ............ | 623/17.16 |
| 6,156,067 A * | 12/2000 | Bryan et al. ............... | 623/17.15 |
| 6,344,057 B1 * | 2/2002 | Rabbe et al. ............... | 623/17.11 |
| 2004/0249462 A1 * | 12/2004 | Huang ....................... | 623/17.13 |

FOREIGN PATENT DOCUMENTS

| | | |
|---|---|---|
| DE | 200 19 520 U1 | 2/2001 |
| DE | 101 30 825 A1 | 3/2002 |
| EP | 0 621 020 A1 | 10/1994 |
| EP | 1 417 940 A1 | 11/2002 |
| EP | 1 290 993 A1 | 3/2003 |

\* cited by examiner

*Primary Examiner* — Eduardo C Robert
*Assistant Examiner* — Tara Carter
(74) *Attorney, Agent, or Firm* — Davis & Bujold, P.L.L.C.

(57) ABSTRACT

A spinal prosthesis has a prosthetic vertebral body in the form of a hollow cylinder (1) with perforated wall and attached prosthetic intervertebral discs formed by springs (7,8) molded into silicone-rubber beads (9,10). Anchoring of the cylinder (1) to the damaged vertebra (II) is by means of entrapment of an elongate lug (12) of the cylinder 1 within a slot (16) of a plate (11) retained by screws (12) within a recess (13) of the damaged vertebra (II). The springs (7,8) of the resilient beads (9,10) are attached to the natural vertebrae (I,III) superior and inferior to the damaged vertebra (II) by fixing plates (3,4) which have flanges (20,21) that are held by screws (22) to those vertebrae (I,III). Where adjoining vertebrae are damaged, two or more prosthetic cylinders (1) for anchoring to the individual vertebra are used with interconnecting resilient beads (9;10).

14 Claims, 5 Drawing Sheets

SPINAL PROSTHESES

This application is a national stage completion of PCT/GB2005/004486 filed Nov. 21, 2005 which claims priority from British Application Serial No. 0425546.9 filed Nov. 20, 2004.

FIELD OF THE INVENTION

This invention relates to spinal prostheses.

SUMMARY OF THE INVENTION

According to the present invention there is provided a spinal prosthesis comprising a prosthetic vertebral body having means for attaching it to a subject vertebra, two resilient elements attached to opposite ends of the prosthetic vertebral body to provide respectively prosthetic intervertebral discs between the subject vertebra and the vertebrae superior and inferior to it, and means for attaching the resilient elements to their respective superior and inferior vertebrae.

The spinal prosthesis of the invention is of a form that is readily applicable to replacement of cervical, lower thoracic and lumbar vertebrae and their discs, that have been damaged by fracture or disease. It is of especial advantage in the context of a damaged cervical vertebra, for which the normal surgical practice is to replace it and its discs by a prosthetic vertebra that becomes fused to the natural vertebrae superior and inferior to it. The result is that in addition to the loss of shock absorption in the affected vertebra, there is loss of rotational freedom too with the consequence that the patient loses in part or altogether, the ability to turn the head. This disadvantage can be entirely or largely overcome using the prosthesis of the invention.

The prosthetic vertebral body of the spinal prosthesis of the present invention may be hollow with a perforated wall, for receiving bone chips or bone substitute. It may be cylindrical of circular or other cross-section.

The resilient elements may involve coiled springs, and may each comprise a compression spring embedded in a resilient material, or a bead solely of resilient material. In either case, the resilient material may be silicone rubber.

The means for attaching the two resilient elements to the respective superior and inferior vertebrae may include two fixing plates for screw attachment to the relevant superior and inferior vertebra respectively. One of the resilient elements may, as an alternative where the superior or inferior vertebra is also damaged, be attached to a further prosthetic vertebral body that is attached to that vertebra.

BRIEF DESCRIPTION OF THE DRAWINGS

A spinal prosthesis in accordance with the present invention will now be described, by way of example, with reference to the accompanying drawings, in which.

DETAILED DESCRIPTION OF THE INVENTION

Figure 1:
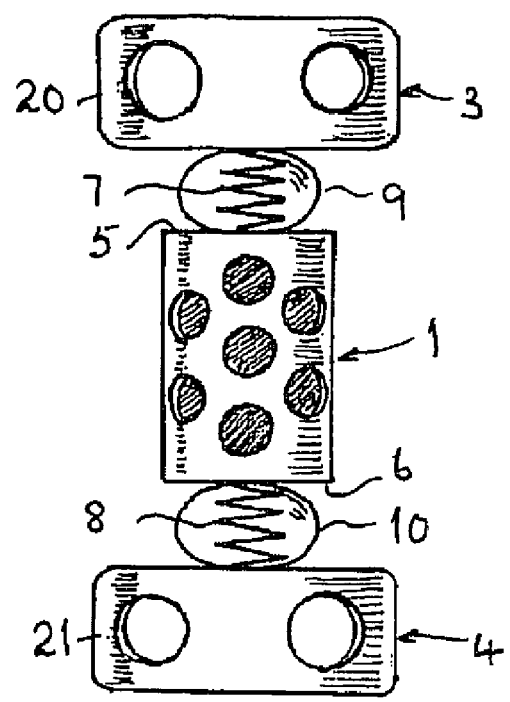
FIGS. 1 to 4 are, respectively, front, rear, side and perspective views of the spinal prosthesis of the invention.
Figure 2:
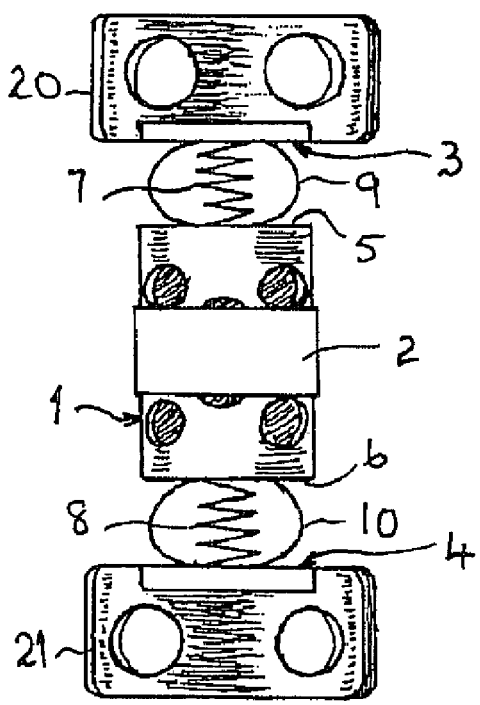
Figure 3:
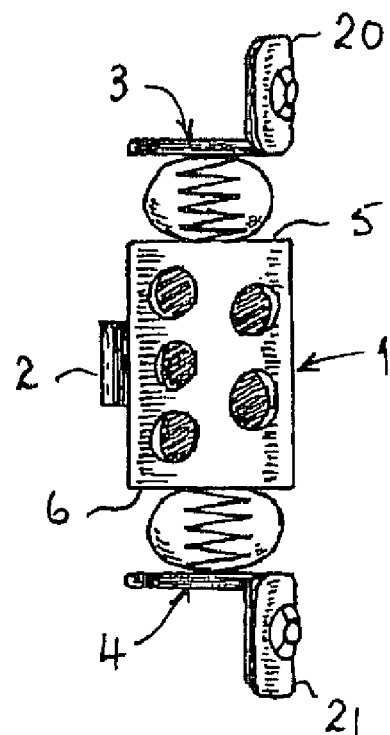
Figure 4:
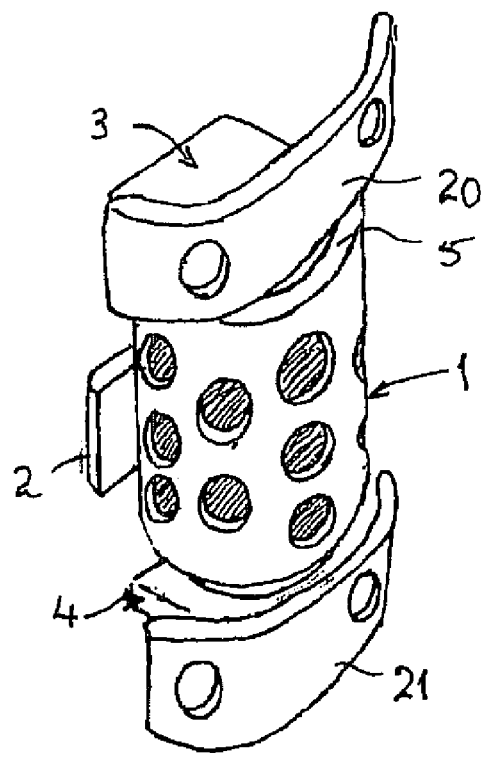

Referring to FIGS. 1 to 4 the spinal prosthesis, which in this case is for replacement of a fractured or otherwise damaged cervical vertebra and its discs, involves a prosthetic vertebral body in the form of a hollow, metal cylinder 1 of circular cross-section having a perforated wall. An elongate anchor lug 2 (FIGS. 2 and 4) is secured to the rear of the cylinder 1 to extend transversely of it, and anchor plates 3 and 4 are attached to end-caps 5 and 6 respectively of the cylinder 1 via individual, coiled compression-springs 7 and 8. The springs 7 and 8 are moulded into respective beads 9 and 10 of silicone rubber.

Figure 5:
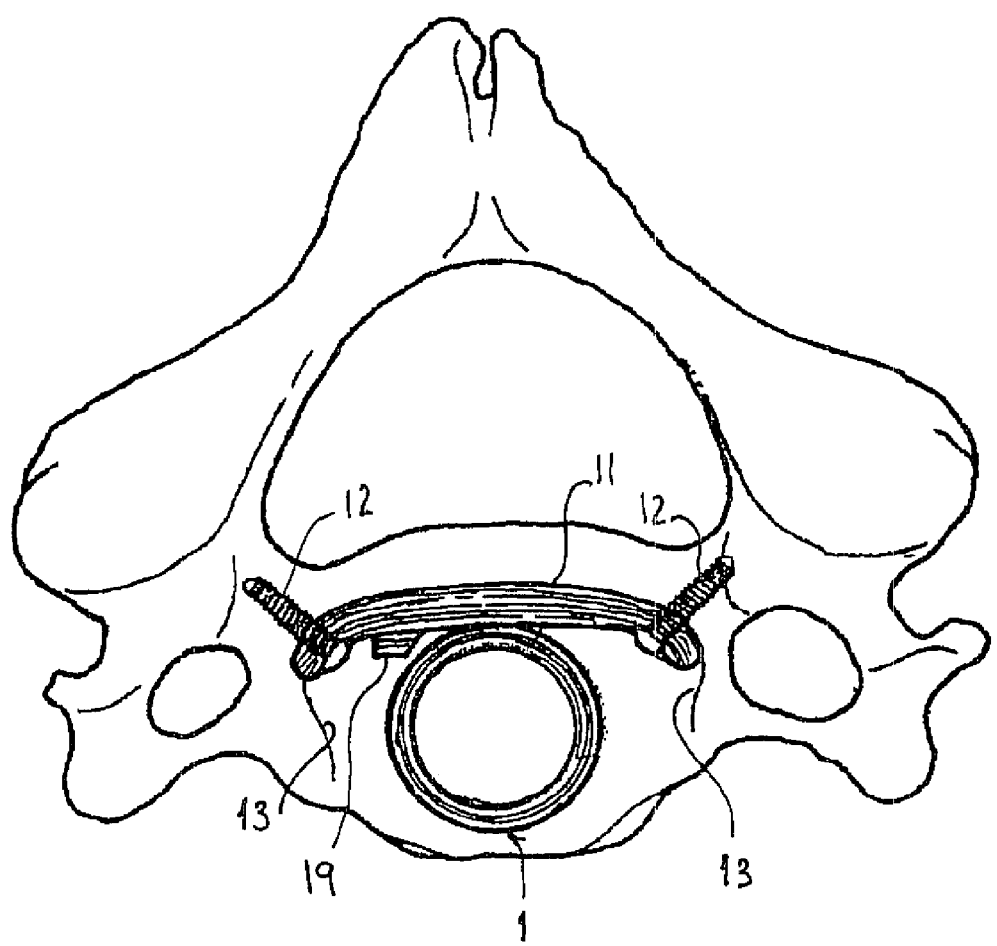
FIG. 5 is a sectional view illustrative of the anchoring of the prosthetic vertebral body of the spinal prosthesis of FIGS. 1 to 4.

Before the prosthetic assembly is implanted, the cylinder 1 is filled with natural bone chips or bone-substitute material, and is closed by screwing or bonding the end-caps 5 and 6 to either end. Additionally, an anterior portion of the damaged vertebra is cut away to accommodate the cylinder 1, and the superior and inferior intervertebral discs are removed. After this, as illustrated in FIG. 5, an elongate fixing plate 11 is secured by screws 12 within the cut-away recess 13 of the damaged vertebra, and the cylinder 1 is anchored to this plate 11 by means of the lug 2.

Figure 6:
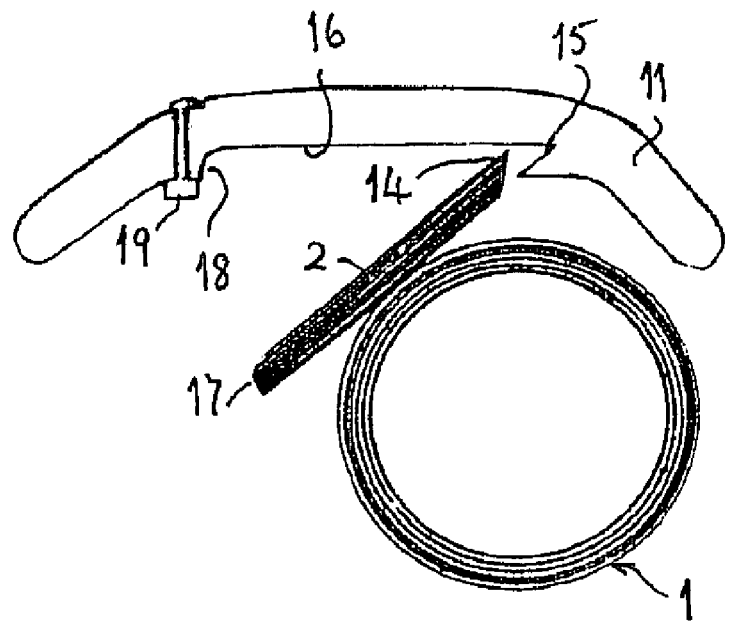
FIGS. 6 and 7 are illustrative of successive stages in bringing about the anchoring of the prosthetic vertebral body illustrated in FIG. 5.
Figure 7:
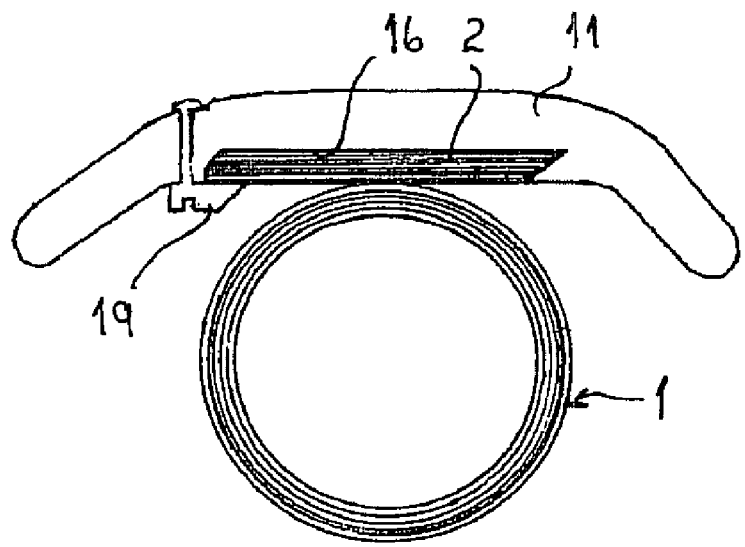

More especially in the latter respect, and as illustrated in FIG. 6, the lug 2 has a bevelled leading-end 14 and the cylinder 1 is moved onto the plate 11 to enter the end 14 into a re-entrant end 15 of a slot 16 in the plate 11. With the leading-end 14 fully engaged in the re-entrant end 15, the trailing-end 17 of the lug 2 is now brought into the other end 18 of the slot 16 so as to nest the lug 2 fully within the slot 16. In this condition, a turn-screw 19 at the end 18 of the slot 16 is turned through half a turn to overlie the lug 2, as illustrated in FIG. 7, trapping it securely, and with it the cylinder 1, to the plate 11.

Figure 8:
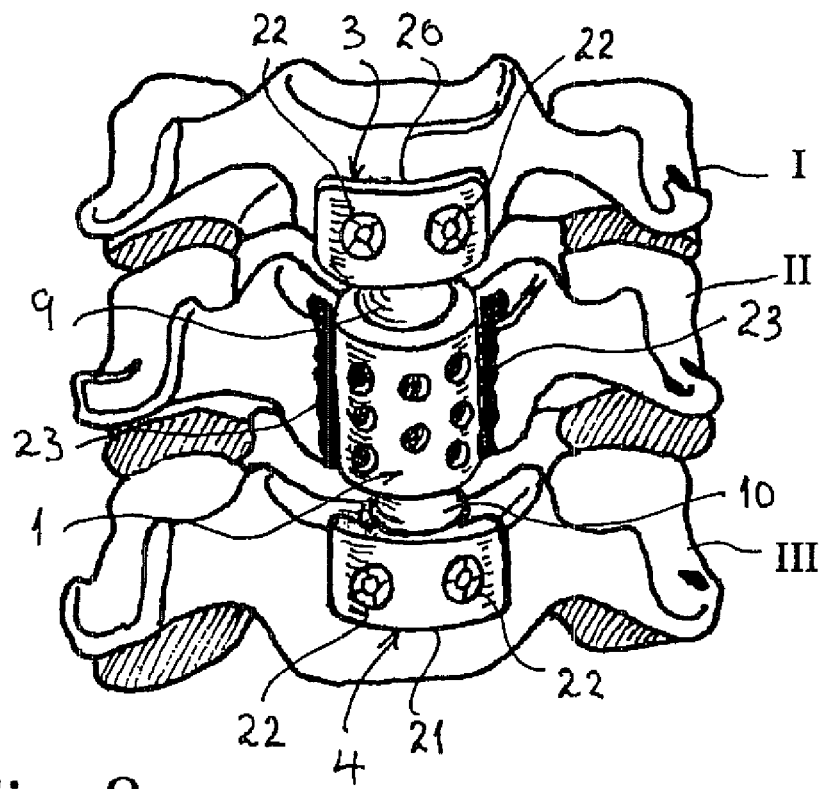
FIGS. 8 and 9 are anterior and lateral views respectively of the implanted spinal prosthesis of FIGS. 1 to 4.
Figure 9:
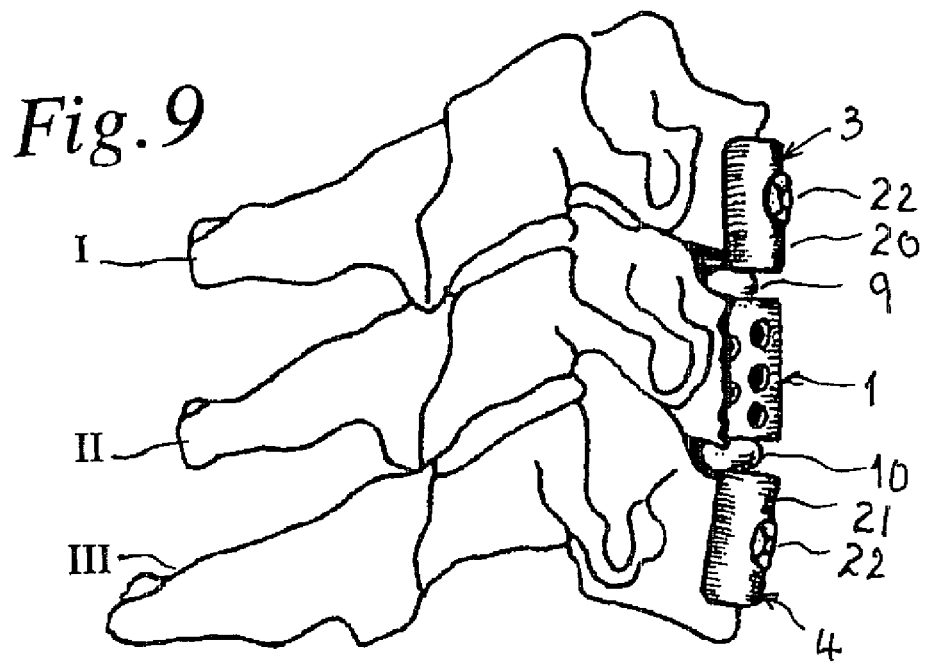

Referring now also to FIGS. 8 and 9, the anchor plates 3 and 4 are secured respectively to the vertebrae I and III superior and inferior to the damaged vertebra II, with the beads 9 and 10 eased into the spaces left by the removed intervertebral discs. More particularly, curved flanges 20 and 21 of the plates 3 and 4 respectively abut the anterior faces of the natural vertebrae I and III and are firmly secured to them by screws 22.

After the prosthetic vertebral body formed by the cylinder 1 has been anchored and the prosthetic intervertebral discs formed by the beads 9 and 10 have been secured as described above, there will eventually be fusion of the bone chips or substitute bone within the cylinder 1. This will extend through the perforated wall of the cylinder 1 to the remaining part of the damaged vertebra II, and will be effective to restore to a large extent the original vertebral structure. The fusion can be enhanced by packing further bone chips or bone substitute around the cylinder 1 within the recess 13 as illustrated at 23 in FIG. 8.

The form of prosthetic vertebra described above has the advantage that there is no fusion or locking together of vertebrae, and the natural degrees of flexion and extension together with rotation can be to a large extent preserved. The artificial discs formed by the beads 9 and 10 incorporating the springs 7 and 8 allow for relative vertebral movement. The springs 7 and 8 in particular are strong enough for the required load-bearing, and together with the silicone rubber in which they are moulded, provide a substantial degree of resilience for cushioning purposes. The fact that the beads 9 and 10 are attached through the plates 3 and 4 to the superior and inferior vertebrae I and III, as well as to the cylinder 1 ensures that they are securely retained in proper place.

The entire prosthetic complex of vertebral body and intervertebral discs formed by the cylinder 1 and attached beads 9 and 10, may be readily released for removal if this should be required, simply by unscrewing the four screws 22 and turning the screw 19 back from its overlapping position. The screws 12 may also be unscrewed for removal of the plate 11.

Although the prosthetic vertebral body described above is a cylinder 1 of circular cross-section, the cross-section may be different from this and indeed may be more oval so as to be more closely comparable with that of the natural vertebra. Furthermore, although the cylinder 1 is hollow and has a perforated wall, it may instead be a short length of tube with an imperforate wall, or a short length of rod, fusing of the tube or rod into the body of the vertebra may be enhanced in these circumstances by bone chips or bone substrate packed round it.

It is not necessary that the beads 9 and 10 incorporate discrete springs 7 and 8, in that they may instead be provided by solid beads wholly of silicone rubber or other resilient plastics material.

The invention has been described above in the context of cervical-vertebral prosthesis. Essentially the same principles of construction may be used for prosthesis of lower thoracic and lumbar vertebrae. Furthermore, although the prosthesis described is for use in connection with a single damaged vertebra, the same basic form may be extended for use where two or more adjoining vertebrae are damaged.

For example, a chain of two or more cylinders or other prosthetic vertebral bodies corresponding to the cylinder 1, may be used, each being attached to the next via a bead corresponding to the bead 9 (or 10) for use as the intervening disc. Each of the two end vertebral bodies of such a chain would be attached to a plate corresponding to the plate 3 (or 4), via a bead corresponding to the bead 9 (or 10).

The invention claimed is:

1. A spinal prosthesis comprising:
a prosthetic vertebral body, the prosthetic vertebral body for replacement of a vertebral body of a subject vertebra, the prosthetic vertebral body having posterior anchoring means located posteriorly of the prosthetic vertebral body for anchoring the spinal prosthesis to the subject vertebra;
first and second resilient elements attached to opposite ends of the prosthetic vertebral body, the first resilient element providing a prosthetic intervertebral disc for location between the subject vertebra and a superior vertebra, and the second resilient element providing a prosthetic intervertebral disc for location between the subject vertebra and an inferior vertebra; and
attaching means anterior of the prosthetic vertebral body for attaching the first and the second resilient elements to anterior aspects of the superior and the inferior vertebrae respectively;
wherein the posterior anchoring means is configured to contact the subject vertebra and comprises a fixing member for attachment by screws to the subject vertebra, and retention means secured to the prosthetic vertebral body posteriorly of the prosthetic vertebral body for engagement with the fixing member in retention of the prosthetic vertebral body anchored to the subject vertebra.

2. The spinal prosthesis according to claim 1, wherein the prosthetic vertebral body is hollow for receiving one of a multiplicity of bone chips and bone substitute, and the prosthetic vertebral body having a perforated wall.

3. The spinal prosthesis according to claim 1, wherein the prosthetic vertebral body is cylindrical.

4. The spinal prosthesis according to claim 1, wherein the prosthetic vertebral body is one of a rod and a tube.

5. A spinal prosthesis comprising;
a prosthetic vertebral body for replacement of a vertebral body of a subject vertebra, the prosthetic vertebral body having posterior anchoring means located posteriorly of the prosthetic vertebral body for anchoring the spinal prosthesis to the subject vertebra;
first and second resilient elements attached to opposite ends of the prosthetic vertebral body, the first resilient element providing a prosthetic intervertebral disc for location between the subject vertebra and a superior vertebra, and the second resilient element providing a prosthetic intervertebral disc for location between the subject vertebra and an inferior vertebra; and
attaching means anterior of the prosthetic vertebral body for attaching the first and the second resilient elements to anterior aspects of the superior and the inferior vertebrae respectively;
wherein the anchoring means is configured to directly contact the subject vertebra and comprises a fixing plate for securing to the subject vertebra, and retention means secured to the prosthetic vertebral body posteriorly of the prosthetic vertebral body for engagement with the secured fixing plate in retention of the prosthetic vertebral body anchored to the subject vertebra.

6. The spinal prosthesis according to claim 5, wherein the retention means secured to the prosthetic vertebral body comprises an anchor lug secured to the prosthetic vertebral body posteriorly of the prosthetic vertebral body for engagement with the fixing plate, and a selectively-operable device for retention of the anchor lug anchored to the fixing plate.

7. The spinal prosthesis according to claim 6, wherein the anchor lug is elongate and the fixing plate has an elongate slot for receiving the anchor lug nested lengthwise within it, and the selectively-operable device is operable to trap the anchor lug within the slot.

8. The spinal prosthesis according to claim 5, wherein the resilient elements comprise coiled springs.

9. The spinal prosthesis according to claim 8, wherein each of the resilient elements comprises a compression spring embedded in a resilient material.

10. The spinal prosthesis according to claim 9, wherein the resilient elements comprise beads of resilient material.

11. The spinal prosthesis according to claim 9, wherein the resilient material is silicone rubber.

12. The spinal prosthesis according to claim 5, wherein the means for attaching the first and the second resilient elements to the superior and the inferior vertebrae respectively, comprises two fixing plates for screw attachment to the superior and the inferior vertebrae, respectively.

13. The spinal prosthesis according to claim 5, wherein the spinal prosthetic body is attached by a resilient element to a further prosthetic vertebral body.

14. A spinal prosthesis comprising a prosthetic vertebral body, the prosthetic vertebral body having anchoring means for anchoring the spinal prosthesis to a subject vertebra, first and second resilient elements attached to opposite ends of the prosthetic vertebral body, the first resilient element providing a prosthetic intervertebral disc for location between the subject vertebra and a superior vertebra, and the second resilient element providing a prosthetic intervertebral disc for location between the subject vertebra and an inferior vertebra, and means for attaching the first and second resilient elements to the superior and inferior vertebrae respectively;
the anchoring means comprises a fixing plate for securing to the subject vertebra, and means carried by the prosthetic vertebral body for engagement with the secured fixing plate in retention of the prosthetic vertebral body anchored to the subject vertebra;
the means carried by the prosthetic vertebral body comprises an anchor lug secured to the prosthetic vertebral body for engagement with the fixing plate, and a selectively-operable device for retention of the anchor lug anchored to the fixing plate;
the anchor lug is elongate and the fixing plate has an elongate slot for receiving the anchor lug nested lengthwise therein, and the selectively-operable device is operable to trap the anchor lug within the elongate slot; and the anchor lug has two ends, the elongate slot has a re-entrant end for trapping a first of the two ends of the anchor lug within the elongate slot, and the selectively-operable device is operable to trap the second of the two ends of the anchor lug within the elongate slot.

* * * * *